United States Patent
Maki, Jr. et al.

(10) Patent No.: US 6,269,684 B1
(45) Date of Patent: Aug. 7, 2001

(54) DYNAMIC FLUID LOSS CELL APPARATUS AND METHOD THEREOF

(75) Inventors: Voldi E. Maki, Jr., Austin; Fred L. Sabins, Sugarland, both of TX (US)

(73) Assignee: Halliburton Engergy Services, Inc., Houston, TX (US)

( * ) Notice: Subject to any disclaimer, the term of this patent is extended or adjusted under 35 U.S.C. 154(b) by 0 days.

(21) Appl. No.: 09/166,456

(22) Filed: Oct. 5, 1998

(51) Int. Cl.$^7$ ...................................... E21B 49/10
(52) U.S. Cl. .................. 73/53.01; 73/61.71; 73/61.72; 73/865.6
(58) Field of Search .............. 73/61.71, 61.72, 73/53.01, 61.41, 865.6

(56) References Cited

U.S. PATENT DOCUMENTS

| | | | |
|---|---|---|---|
| 3,286,510 | 11/1966 | Parker | 73/54.02 |
| 3,289,467 | * 12/1966 | Parker et al. | 73/61.63 |
| 4,259,868 | 4/1981 | Rao et al. | 73/597 |
| 4,380,266 | 4/1983 | Wellington . | |
| 4,409,662 | 10/1983 | Rao . | |
| 4,430,889 | 2/1984 | Sutton | 73/865.6 |
| 4,528,842 | * 7/1985 | Brown | 73/865.6 X |
| 4,567,765 | 2/1986 | Rao et al. . | |
| 4,648,264 | 3/1987 | Freese et al. . | |
| 4,691,558 | 9/1987 | Vinson et al. . | |
| 4,700,567 | 10/1987 | Frey et al. . | |
| 4,780,858 | 10/1988 | Clerke . | |
| 4,823,594 | 4/1989 | Gray . | |
| 5,325,723 | 7/1994 | Meadows et al. . | |
| 5,329,811 | 7/1994 | Schultz et al. . | |

FOREIGN PATENT DOCUMENTS

2017916  * 10/1979  (GB) ................................... 73/865.6

OTHER PUBLICATIONS

J.V. Fisk et al.: "The Use of Filtration Theory in Developing a Mechanism for Filter–Cake Deposition by Drilling Fluids in Laminar Flow," SPE Drilling Engineering, Sep. 1991, pp. 196–202.

Marlo Zamora et al.: "Innovative Devices for Testing Drilling Muds," SPE Drilling Engineering, Mar. 1990, pp. 11–16.

B.G. Chester, "Dynamics and Static Filtrate–Loss Techniques for Monitoring Filter–Cake Quality Improves Drilling–Fluid Performance," SPE Drilling & Conference, Mar. 18, 1994.

* cited by examiner

*Primary Examiner*—Daniel S. Larkin
(74) *Attorney, Agent, or Firm*—Browning Bushman

(57) ABSTRACT

A dynamic fluid loss cell apparatus and method for measuring filter-cake build-up on a simulated core of the well-bore and for measuring the effectiveness of a spacer fluid to remove filter-cake. There is also provided, a dynamic fluid loss cell apparatus and method for measuring the dynamic fluid loss during the simulated build-up and removal of the filter-cake. The apparatus and method further provides for performing the measurements under various conditions including temperature and differential pressure.

17 Claims, 6 Drawing Sheets

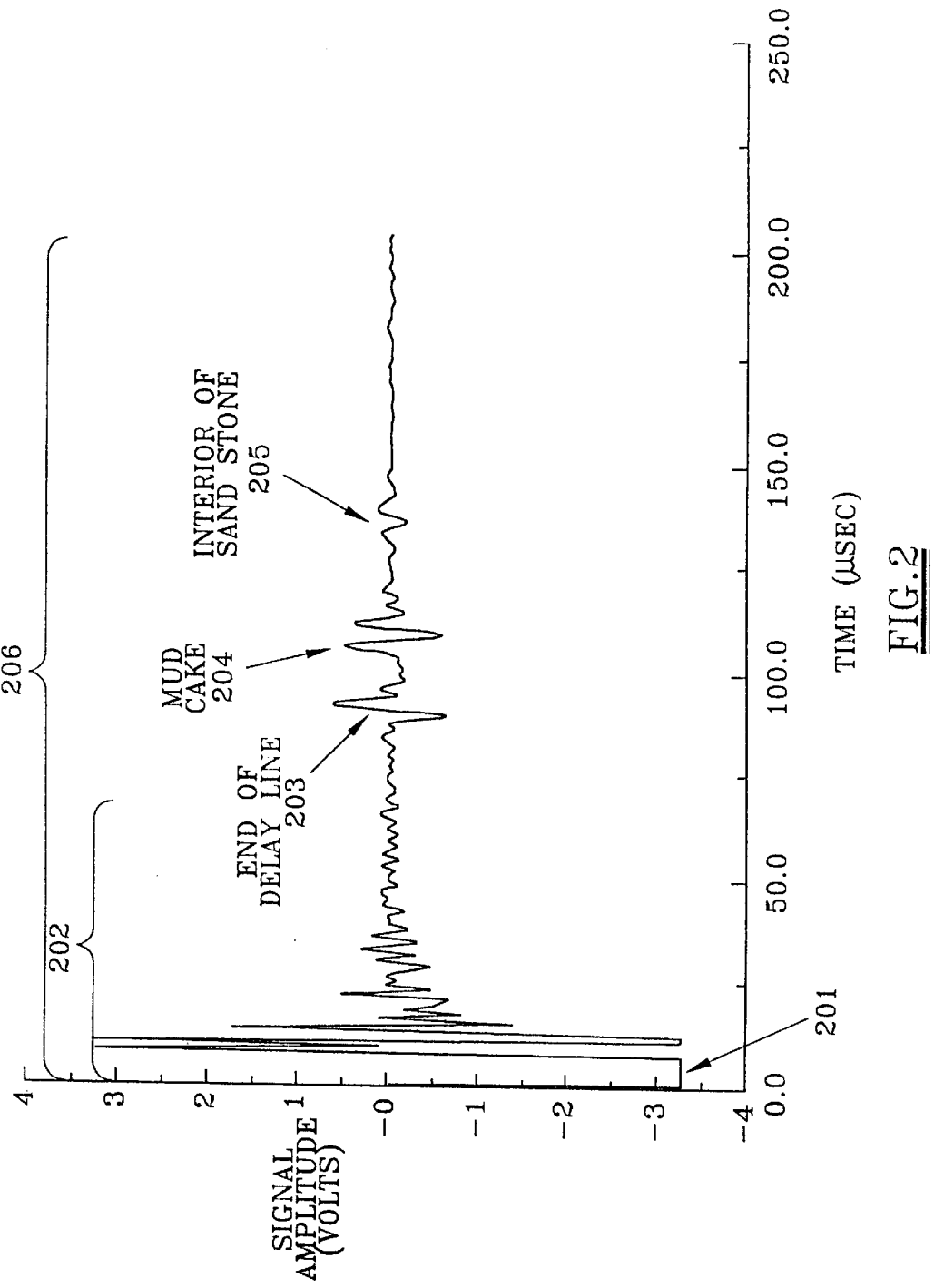

DYNAMIC FLUID LOSS CELL APPARATUS AND METHOD THEREOF

TECHNICAL FIELD

The present invention relates in general to a dynamic fluid loss cell apparatus and method, and in particular, a dynamic fluid loss cell apparatus and method for dynamically simulating the build-up and removal of filter-cake on the interior of a well-bore in oil and gas wells and the loss of fluids into the interior of a well-bore in oil and gas wells.

BACKGROUND INFORMATION

When drilling oil and gas wells, drilling fluids are used to maintain pressure at the bottom of the well to keep fluids from the formation from flowing into the well-bore. This drilling fluid may be water or oil based and is often referred to as mud or drilling mud. The drilling fluid is designed to have a density or weight so that the column of drilling fluid achieves a pressure slightly greater than the formation pressure encountered while drilling. As a well is drilled, the higher pressure from the well-bore forces fluid in the drilling fluid into the formation. Fluid from the drilling fluid driven into the formation by differential pressure causes the particles in the drilling fluid to be left on the wall of the well-bore. This layer of particles is the filter-cake. The build-up of this filter-cake on a well-bore causes difficulties. For instance, the filter-cake on the well-bore makes it difficult for cement to seal against the formation and can potentially compromise the zone isolation. Accordingly, special fluids, sometimes referred to as spacer fluids, are pumped into the well to remove the filter-cake. These spacer fluids may contain surfactants or emulsifiers to assist in this removal.

In addition to causing filter-cake to build, the fluid loss into the formation of the drilling fluids, as well as the fluid loss from the spacer, can also cause potential difficulties. For instance, these fluids lost into the formation can cause near well-born skin damage.

Because the drilling fluids and spacer fluids are variable, it is desirable to use drilling fluids that will minimize the build-up and spacer fluids that will maximize the removal of the resultant filter-cake. Coordinately, there is a need to use drilling fluids and spacer fluids that minimize the amount of fluid loss into the formation. The characteristics of the filter-cake are determined by the formation, the rheology of the drilling fluid, the temperature, the differential pressure at the surface of the formation (the difference between the pressure of the drilling fluid column and the formation), and by the flow velocity of the drilling fluid. Furthermore, the effectiveness of the spacer fluids is also affected by these same factors including the temperature, differential pressure, and by the flow velocity. The effectiveness of the spacer fluids is also affected by the factors that caused the build-up of the filter-cake. Accordingly, there is a need to simulate the build-up and removal of the filter-cake on the well-bore and the fluid loss into the formation so that more optimal drilling fluids and spacer fluids are used. And, since one of these characteristics is the flow velocity (i.e. the fluids are being circulated during operation), there is also a need to simulate the build-up and removal of filter-cake and fluid loss under dynamic conditions.

Therefore, there is a need in the art for a dynamic fluid loss cell apparatus and method, which is an apparatus and method that simulates the build-up and removal of filter-cake on the interior of a well-bore in oil and gas wells dynamically.

SUMMARY OF THE INVENTION

The aforementioned needs are addressed by the present invention. Accordingly, there is provided a dynamic fluid loss cell apparatus and method for measuring filter-cake build-up on a simulated core of the well-bore and for measuring the effectiveness of a spacer fluid to remove filter-cake. There is also provided, a dynamic fluid loss cell apparatus and method for measuring the dynamic fluid loss during the simulated build-up and removal of the filter-cake. The apparatus and method further provides for performing the measurements under various conditions including temperature and differential pressure.

The present invention has an advantage of performing the simulation on cores of the formation, generally taken from a nearby oil and gas well, to assist in the selection of better drilling fluids and spacer fluids prior to using these fluids during drilling operations. Furthermore, the present invention has an advantage of performing the simulation on cores taken from the actual oil and gas well itself, prior to pumping the spacer fluids. This would again assist in the selection of better spacer fluids to use.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 2 illustrates, in graphical form, an acoustic signal recorded in accordance with the present invention;

DETAILED DESCRIPTION

Figure 1:
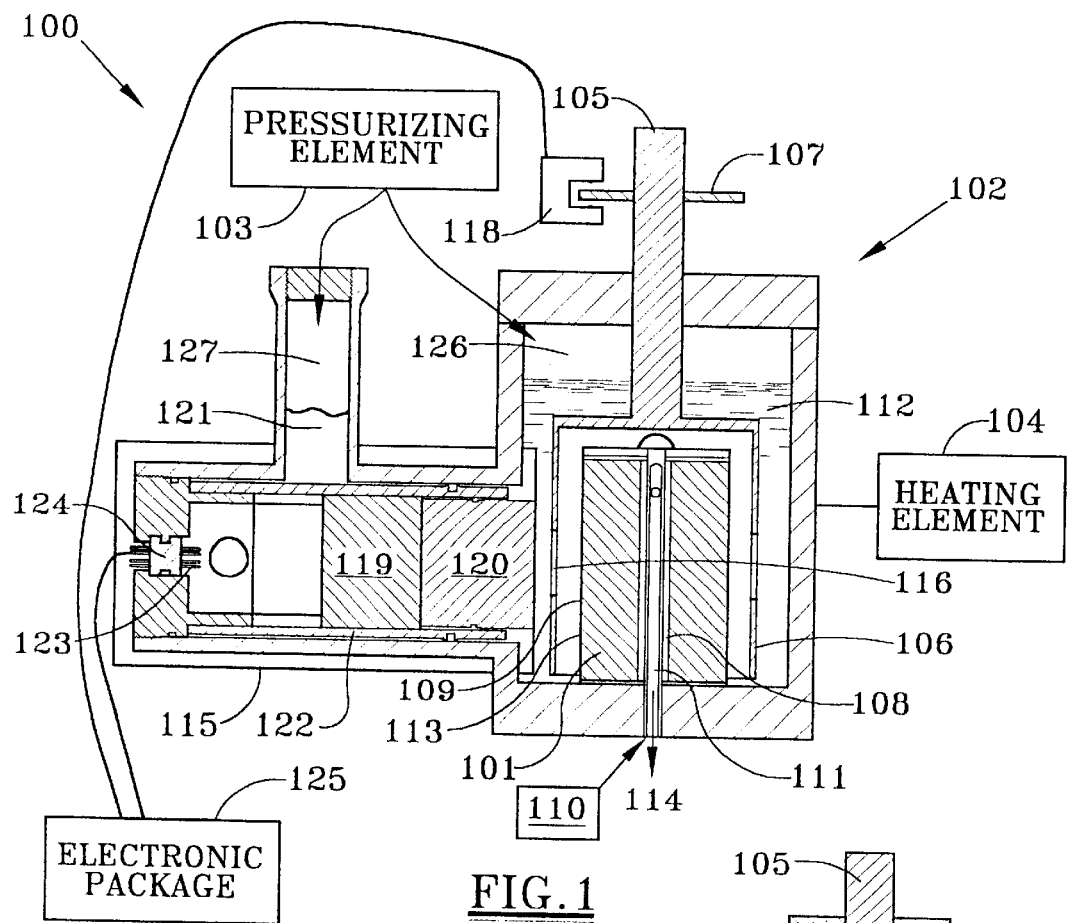
FIG. 1 illustrates, in block diagram form, a dynamic fluid loss cell apparatus in accordance with an embodiment of the present invention.

The present invention provides a method and apparatus for simulating the build-up and removal of filter-cake from the interior of an oil and gas well-bore. A simulated core of a well-bore is placed into the dynamic fluid loss cell apparatus, which then subjects the simulated core to the dynamic conditions it would experience during drilling operations. The thickness of the filter-cake is measured as it builds-up and is removed on the side of the simulated core. Additionally, if desired, the amount of fluids lost into the simulated core may also be measured. As used herein, a simulated core is a core that simulates the formation of the oil and gas well-bore. Such a simulated core (or sample core) may include, amongst other things, a natural core (such as a core from the well-bore being evaluated, a core of a well drilled in the same formation as the well-bore being evaluated or, a core of well drilled in a different formation as the well being evaluated), or an artificial core.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

Refer now to the drawings wherein depicted elements are not necessarily shown to scale and wherein like or similar elements are designated by the same reference numeral through the several views.

Figure 1A:
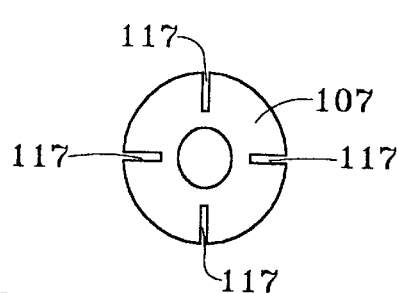
FIG. 1A illustrates, in block diagram form, an overhead view of a rotation wheel in accordance with an embodiment of the present invention.
Figure 1B:
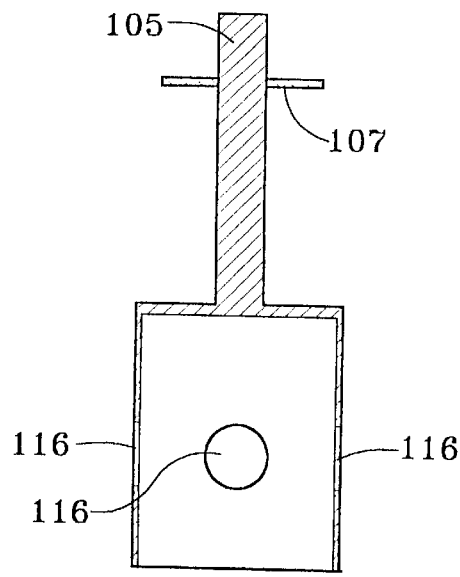
FIG. 1B illustrates, in block diagram form, a side view of the rotating sleeve showing the acoustic window in accordance with an embodiment of the present invention.

Refer first to FIGS. 1, 1A, and 1B illustrating a dynamic fluid loss cell apparatus 100 in accordance with an embodiment of the present invention. The dynamic fluid loss cell apparatus has an enclosed cell, such as a high pressure cell 102, in which an object, such as a simulated core 101, may be received. A simulated core 101 is well known in the art and is typically shaped in a hollow cylinder form so that it has a simulated core exterior surface 109 and a simulated core center 108. The simulated core 101 may be a core taken from a well drilled in close proximity to the formation that simulated core 101 is to simulate. The simulated core 101 may also be a manufactured material that behaves in a manner similar to a sample from a natural formation. Examples of such a simulated core is a sandstone.

As illustrated in FIG. 1, the high pressure cell 102 may receive a fluid 112 such that the simulated core 101 is immersed by fluid 112. When the present invention is being utilized to simulate the build-up of filter-cake, fluid 112 is a drilling fluid 112. When the present invention is being utilized to simulate the removal of filter-cake, fluid 112 is a spacer fluid 112.

The high pressure cell 102 is connected to a pressurizing element 103 to control the pressure inside the high pressure cell 102 and outside the simulated core exterior surface 109. The pressure can be controlled by pressurizing the high pressure cell 102 with a gas 126, such as nitrogen. Such a pressurizing element 103 is well known in the art. The high pressure cell 102 can be pressurized up to 1000 psi during operation of the dynamic fluid loss cell apparatus 100.

The high pressure cell 102 can also be heated by a heating element 104. Such a heating element 104 is well known in the art. The high pressure cell 102 can be heated up to a temperature of 350° F.

The simulated core 101 is received within the high pressure cell 102, so that the simulated core center 108 is operatively connected to a fluid discharge, such as a filtrate conduit 111, that allows filtrate 114 to flow from the simulated core center 108 outside the high pressure cell 102.

Filtrate conduit 111 allows the simulated core center 108 to have a different pressure than the simulated core exterior surface 109. This difference in pressure is the differential pressure. The differential pressure between the simulated core exterior surface 109 and the simulated core center 108 is what causes the fluid inside the high pressure cell 102, such as drilling fluid 112, to attempt to flow from the simulated exterior surface 109, through the simulated core 101, to the simulated core center 108. If desired, a second pressurizing element 110 can be operatively attached to pressurize the simulated core center 108. This may be done by attaching a second pressurizing element 110 to the filtrate conduit 111.

Pressurizing the simulated core center 108 to the same pressure as the simulated core exterior surface 109 will cause the pressure differential to be zero, and the fluid 112 will not attempt to flow through simulated core 101. By doing this, this will allow the pressurization of the high pressure cell 102 without initiating the build-up or removal of the filter-cake 113 at the simulated core exterior surface 109. Build-up or removal of the filter-cake 113 can then be initiated by increasing the pressure with pressurizing element 103 or decreasing the pressure by bleeding off pressure from the simulated core center 108.

The simulated core 101 is received within the high pressure cell 102 so that a flow mechanism, such as a rotatable rotating sleeve 106, may cause the drilling fluid 112 to flow about the simulated core exterior surface 109. A rotation registration wheel 107 can rotate to turn a drive shaft 105 which in turn will rotate the rotating sleeve 106. A motor for driving drive shaft 105 is not shown for sake of simplicity.

To simulate the dynamic building of filter-cake 113 at the simulated exterior surface 109, the dynamic fluid loss cell 100 can be operated as follows. A simulated core 101 is inserted within the high pressure cell 102. For instance, a sandstone core can be used. The high pressure cell 102 is then filled with a desired drilling fluid 112, such as a 17.5 pounds per gallon oil based mud. The rotating sleeve 106 is rotated, such as at 400 rpm. If desired, the heating element 104 heats the drilling mud 112 in the high pressure cell 102, such as at 141° F. However, if operating under ambient temperatures, heating element 104 need not be utilized. The pressurizing element 103 pressurizes the drilling mud 112 in the high pressure cell 102 (and possibly pressurizing element 110 pressurizes the simulated core center 108) to cause a desired pressure differential, such as 400 psi.

Because the pressure differential causes the drilling fluid 112 to attempt to flow through the simulated core 101, fluid passes through the simulated core 101, into the simulated core center 108, and out the filtrate conduit 111. This flow results in the development of a filter-cake 113 on the simulated core exterior surface 109. As previously noted, the characteristics of filter-cake 113 are determined by the simulated core 101, the rheology of the drilling fluid 112, the temperature (caused by heating with heating element 104), the differential pressure (caused by pressurizing with pressurizing element 103 and possibly pressurizing element 110), and by the flow velocity of the drilling fluid 112 (caused by the rotating sleeve 106).

To simulate the dynamic removal of filter-cake 113 at the simulated exterior surface 109, the dynamic fluid loss cell 100 can be operated similarly as above, except that drilling fluid 112 is replaced with a spacer fluid 112. Again, the effectiveness of the spacer fluid is also affected by these same factors including the temperature, the differential pressure, and by the flow velocity. The effectiveness of the spacer fluid is also affected by the build-up of the filter-cake.

The fluid loss of the drilling fluid 112 is measured by measuring the amount of filtrate 114, which is the fluid that flows out of the high pressure cell 102 through the filtrate conduit 111. The accumulation of filtrate 114 may be measured over time.

To measure the build-up and removal of the filter-cake over time, a measuring device, such as an acoustic device 115, is implemented. The acoustic device 115 utilizes a pulse echo measurement to measure the thickness of the filter-cake 113. The rotating sleeve 106 has an acoustic window 116, such as a hole in the rotating sleeve 106. If desired, the rotating sleeve can have additional acoustic windows in the rotating sleeve 106 (as shown in FIG. 1B). The acoustic window 116 is placed in the rotating sleeve 106 so that an acoustic signal (a soundwave) may travel through rotating sleeve 106. The location of the acoustic window 106 may be marked outside the high pressure vessel 102 by using a slot 117 on the rotation registration wheel 107, as shown in FIG. 1A. An optical switch 118 operatively connected to the acoustic device 115 is used to indicate to the acoustic device 115 when the acoustic window 116 is opposite the transducer 119 of the acoustic device 115. The optical switch 118 is thus connected electrically in series with the electronic package 125. The transducer 119 then produces an acoustic pulse, which is used to measure the thickness of the filter-cake 113. As the acoustic pulse travels away from the transducer 119, it may be referred to as the transmit pulse. As the acoustic pulse returns to the transducer 119, it may be referred to as the received echo.

The transducer 119 is separated from the drilling fluid 112 (or the spacer fluid 112) in the high pressure cell 102 by a delay line 120. The delay line 120 separates the transmit pulse from the received echo by an adequate time for the residual signal in the transducer 119 to decay sufficiently. The transducer 119 and delay line 120 are in a separate chamber 122 filled with oil 121 at the same pressure as the drilling fluid 112 (or spacer fluid 112). The pressure can be controlled by pressurizing the separate chamber 122 with a gas 127, such as nitrogen. Fluid 127 may be the same fluid 126 used to pressurize the high pressure cell 102, and fluid 127 is pressurized with pressurizing clement 103. The oil 121 provides electric isolation for the electric wires 123 connecting to the transducer 119. The electric wires 123 to the transducer 119 pass through the electric feed 124 to the electronic package 125.

The received echo is received by transducer 119, and transducer 119 sends a recorded acoustic signal representative of the received echo to the electronic package 125. This received acoustic signal sent by the transducer 119 to the electronic package is analog, although the recorded acoustic signal may be digital. The electronic package 125 then processes the received acoustic signal to determine the thickness of the filter-cake 113. It should be understood that the actual process of transmitting a transmit pulse and receiving a received echo, generating a recorded acoustic signal representative of the received echo, and processing the recorded acoustic signal (by electronic package 125) are well known in the art and will not be described further herein. Such an apparatus and method is described in U.S. Pat. No. 5,044,462 issued to Maki, which is incorporated by reference herein.

FIG. 2 shows a typical recorded acoustic signal 206 measured in a 16 pound per gallon water based mud. For this example, the rotating speed of rotating sleeve 106 was 400 rpm and the pressure differential was 400 psi. The transmit pulse occurred at time zero 201. A significant residual signal 202 can be seen from the 0 to 50.0 microseconds ($\mu$sec). The reflection from the end of the delay line 203 is seen at 87.8 microseconds. The reflection 204 from the filter-cake 113 is seen at 103.0 microseconds. This difference in time corresponds to approximately 0.22 inches based upon the sound velocity in the mud. The third reflected signal 205 is the reflection from the simulated core center 108.

Figure 3:
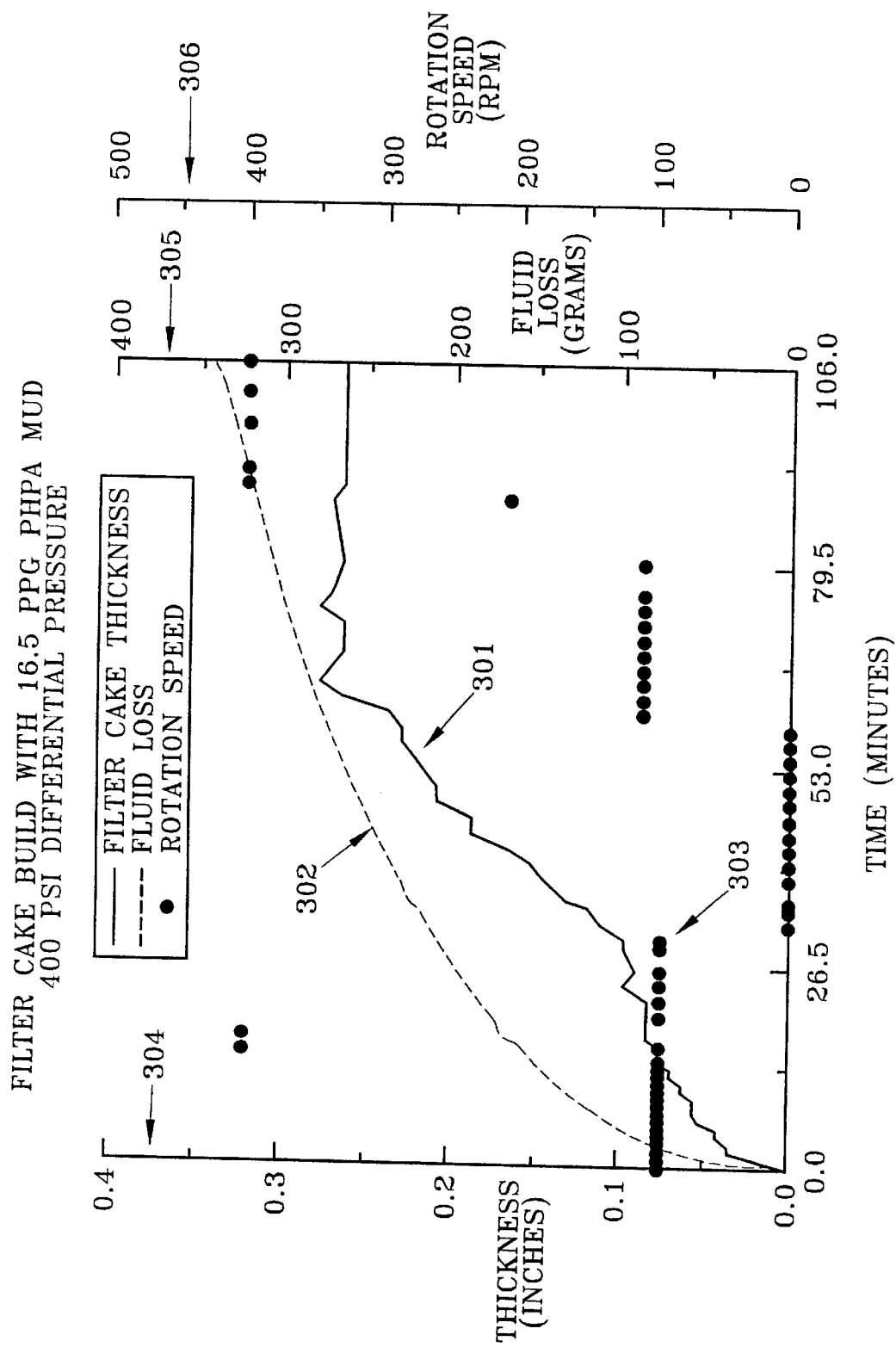
FIG. 3 illustrates, in graphical form, a build-up of filter-cake and fluid loss recorded in accordance with the present invention.

FIG. 3 shows the data of an experiment demonstrating the build-up of filter-cake using a 16.5 pound per gallon PHPA mud. The simulated core 108 was a sandstone. In operation, the drilling mud 112 was placed in the high pressure cell 102 and pressurized. When the pressure on the simulated core center 108 was the same pressure as on the simulated core exterior surface 109, no filter-cake 113 was formed. As the pressure on the simulated core center 108 was lowered to produce a 400 psi pressure differential, fluid moved through the simulated core 101 leaving a filter-cake 113 on the simulated core exterior surface 109. The transducer 119 was first used to measure the location of the simulated core exterior surface 109. Any movement in the travel time then represented the formation of filter-cake 113. During the experiment, the rotating sleeve 106 rotated to created a shearing force on the surface of the forming filter-cake 113. This shearing represented the flow of the drilling fluid 112 in a real well and significantly changed the surface of the filter-cake 113 from what it would have been if the drilling mud 112 had been stagnant.

Referring to FIG. 3, the solid line 301 shows the change in thickness of the filter-cake over time. The scale of the thickness is shown on the left axis 304 (scale from 0.0 to 0.4 inches). The dashed line 302 shows the filtrate 114 which flowed through filtrate conduit 111. The scale of fluid loss is shown on the near right axis 305 (scale from 0 to 400 grams). The solid dots 303 show the rotational speed of rotating sleeve 106 during the experiment. The scale of the rotation speed is shown on the far right axis 306 (scale 0 to 500 rpm). The data of FIG. 3 shows that the fluid loss of the filtrate 114 was slowly decreasing and the thickness of the filter-cake 113 was quickly becoming a maximum. When the rotation of rotation sleeve 106 was stopped, the filter-cake 113 increased quickly in thickness to 0.25 inches although the rate of fluid loss of filtrate 114 showed no significant deviation from its gradual decrease. When the rotation of rotation sleeve 106 was re-initiated, the filter-cake 113 ceased to increase in thickness, however filtrate 114 continued to be produced.

Figure 4:
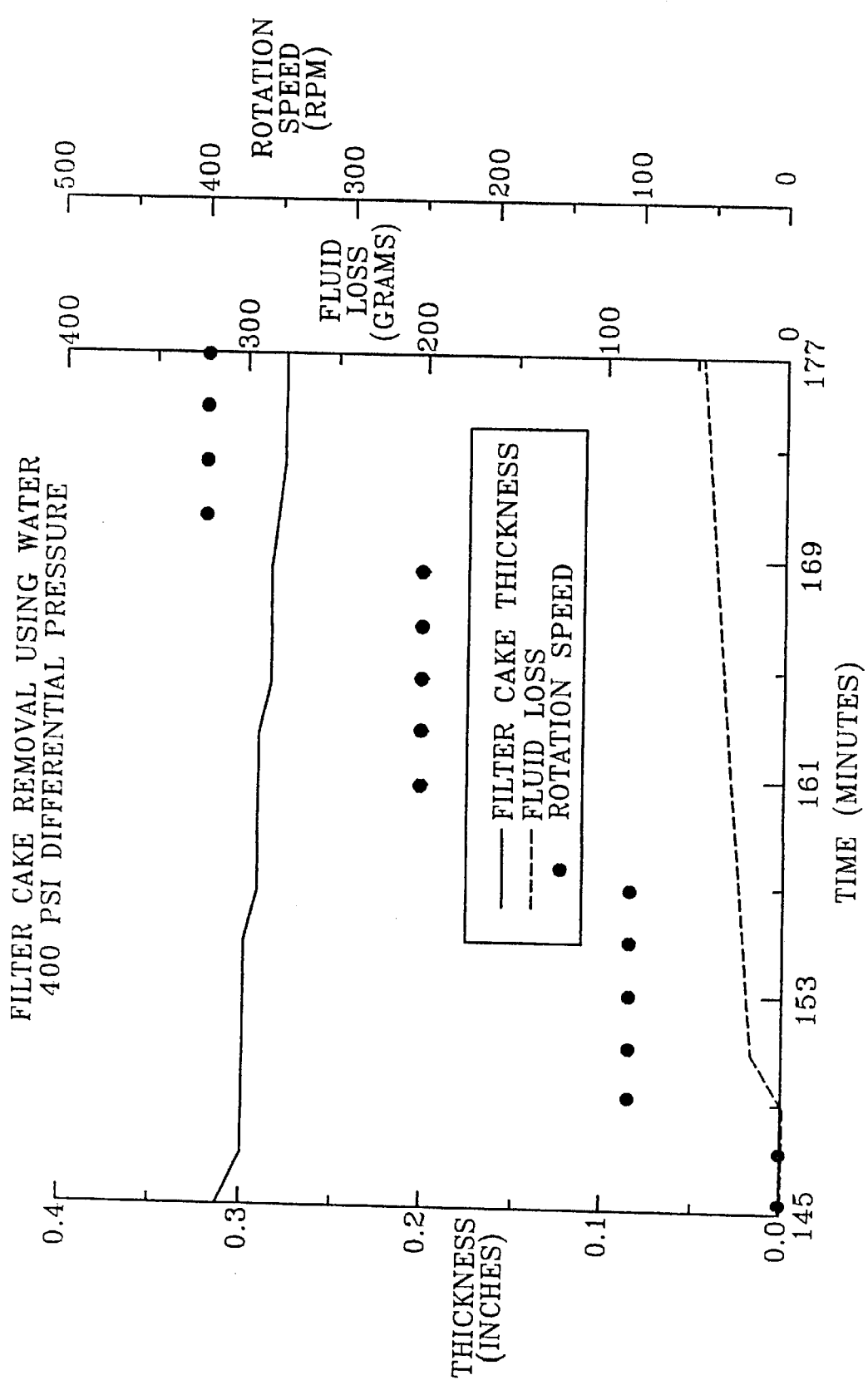
FIG. 4 illustrates, in graphical form, a removal of filter-cake and fluid loss recorded in accordance with the present invention.

FIG. 4 shows the data of the continued experiment as shown in FIG. 3 and demonstrates the removal of the built filter-cake 113. Clear water replaced drilling mud 112 in the high pressure cell 102. The effectiveness of the spacer fluid 112 (the clear water) to remove the filter-cake 113 was similarly measured in real time during this experiment. Again, the pressure differential was 400 psi.

Referring to FIG. 4, the solid line 401 shows the change in thickness of the filter-cake over time. The scale of the thickness is shown on the left axis 404 (scale from 0.0 to 0.4 inches). The dashed line 402 shows the filtrate 114 produced through filtrate conduit 111. The scale of fluid loss is shown on the near right axis 405 (scale from 0 to 400 grams). The solid dots 403 show the rotational speed of rotating sleeve 106 during the experiment. The scale of the rotation speed is shown on the far right axis 406 (scale 0 to 500 rpm).

The data of FIG. 4 shows that filtrate 114 was again produced. During the experiment, the rotation speed of rotation sleeve 106 was varied from 0 to 400 rpm. In this experiment, the filter-cake 113 thickness decreased from 0.3 inches to 0.28 inches while filtrate 114 was produced.

Figure 5:
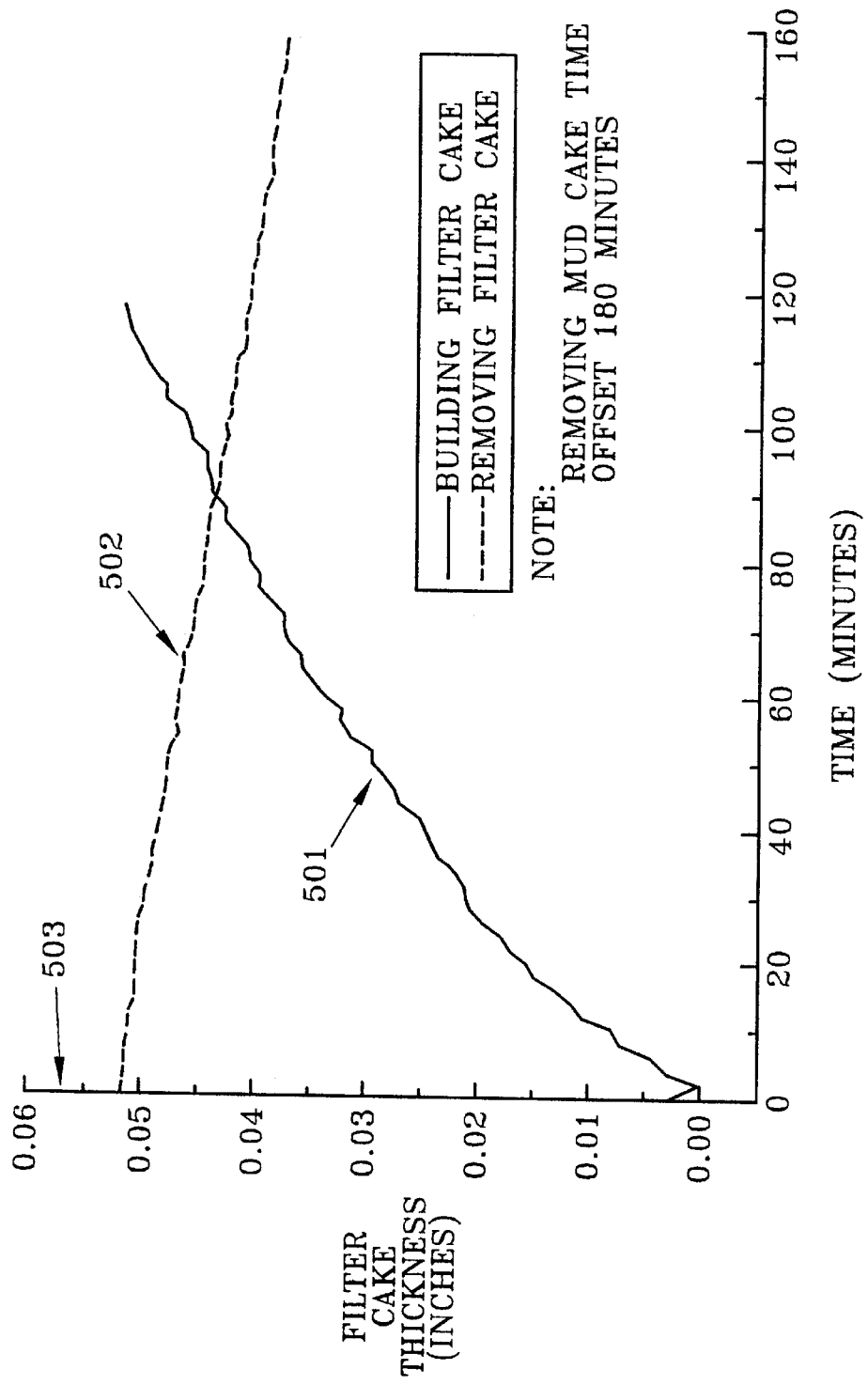
FIG. 5 illustrates, in graphical form, the build-up and removal of filter-cake recorded in accordance with the present invention.

FIG. 5 shows the data of a different experiment demonstrating the build-up and removal of filter-cake using a ligno-sulfonate mud as the drilling fluid 112. The simulated core 101 was sandstone, the pressure differential was 400 psi, and the rotational speed of the rotation sleeve 106 was 400 rpm. Clear water was used as the spacer fluid.

Referring to FIG. 5, the solid line 501 shows the build-up of the filter-cake 113 over time. The dashed line 502 shows the removal of the filter-cake 113 over time. The scale of the filter-cake thickness is shown on the left axis 503 (scale from 0.00 to 0.06 inches). Build-up of the filter-cake 113 began at time zero. Removal of the filter-cake 113 began 180 minutes later. The filter-cake 113 increased to a thickness to about 0.05 inches in 120 minutes. The spacer fluid was then added to remove the filter-cake 113. The spacer fluid removed only about 0.01 inches of the filter-cake in this experiment.

The acoustic properties of the materials used (i.e. delay line 120, fluid 112, simulated core 101) and the filter-cake properties must be considered to determine the requirements of the acoustic measurements. The attenuation of the drilling fluid must be considered. For instance, the attenuation of a 16.5 pound per gallon oil based mud is about 17.5 dB per inch. In the foregoing experiment discussed herein, the nominal travel distance from the delay line face to the core was about one inch. This travel distance results in 35 dB of attenuation. Because of the small impedance contrast between the drilling fluid 112 and the filter-cake 113, only ten percent of the transmit pulse is reflected at the interface between the drilling fluid 112 and the filter-cake 113. This results in another 20-dB drop in signal amplitude. Some of the transmit pulse is reflected at the interface 128 between the delay line 120 and the drilling fluid 112 (or later the spacer fluid 112). The amount of the transmit pulse reflected depends upon the contrast of impedance between the delay line 120 and the drilling fluid 112 (or spacer fluid 112). The amount of transmit pulse reflected reduces the measurement of the transmit pulse propagated into the high pressure cell 102. Another consideration is that the beam width of the acoustic signal must be so small that the transmit pulse will pass through the acoustic window 116 in rotating sleeve 106 without impinging the rotating sleeve 106. Having the transmit pulse reflect from the rotating sleeve 106 would significantly confuse the measurements of the filter-cake 113.

To further achieve the goals of the present invention, a focused transducer 119 can additionally be utilized. Focusing the transducer 119 allows the use of a large, high sensitivity transducer that can produce a narrow beam width. It also allows for a lower frequency of operation, which reduces the attenuation in the drilling fluid 112 (and spacer fluid 112).

The material of delay line 120 is chosen to match as closely as possible the highest attenuation fluid so that as much energy as possible can go into the high pressure cell. One possible embodiment of the transducer 119 is to make it a piece of curved ceramic. Matching curved surfaces of different materials having significantly different coefficients of expansion can be extremely problematic. For the experiments discussed herein, a planar transducer 119 with electronic focusing was used. The electrical focusing is controlled by the electronic package 125. The electronic focusing allows for the ceramic transducer 119 and all interfaces to be flat. The electronic focusing allows for compensation of changes in sound velocity in the delay line 120 with temperature.

In the particular application of the experiments discussed herein, the delay line 120 was made of a synthetic fluorine-containing resin, namely TEFLON, because of TEFLON's acoustic impedance and its resistance to chemicals at high temperatures. The sound velocity of TEFLON changes significantly with temperature.

Figure 6:
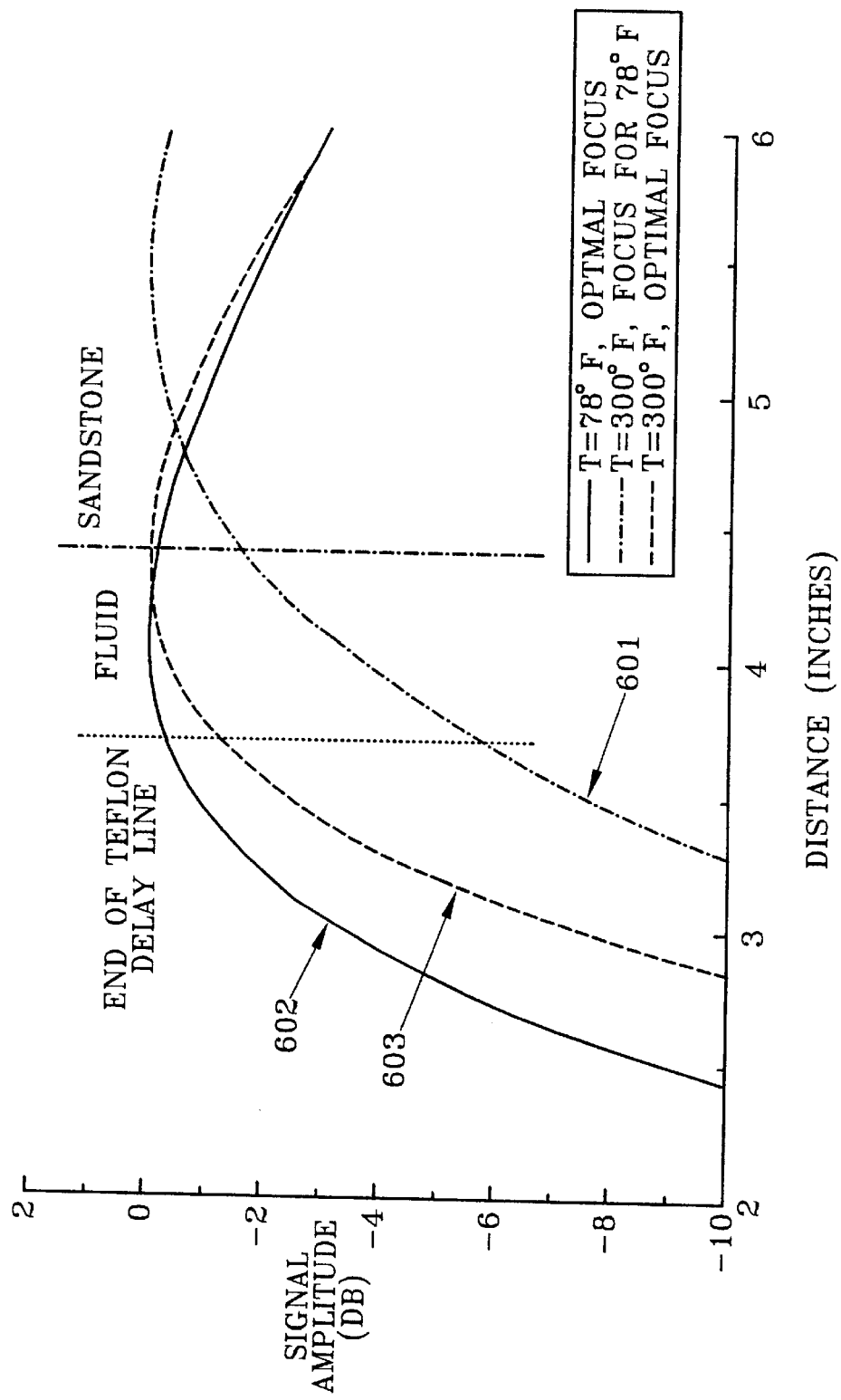
FIG. 6 illustrates, in graphical form, a change in focusing of the acoustic signal launched by the transducer used in accordance with the present invention resulting from changes in sound velocity of the material in the delay line of the transducer.

FIG. 6 shows the change in focusing of an acoustic signal launched by the transducer 119 used in accordance with the present invention resulting from changes in sound velocity of the material in the delay line 120 of the transducer 119. The acoustic device 115 as discussed herein and used in the experiments discussed herein was utilized for the data of FIG. 6.

Referring to FIG. 6, the solid line 602 shows the reflected signal amplitude of the acoustic signal when the temperature of the TEFLON is 78° F. The dashed and dotted line 601 shows the effect of heating the TEFLON to 300° F. without compensation. The dashed line 603 shows the signal amplitude when the focusing is compensated for the change in sound velocity in the TEFLON. Those skilled in the art will understand that TEFLON is a trademark, and that the generic term for the product is tetrafluoroethylene. Electronic focusing allows the acoustic signal to be optimized for the change in velocity in the delay line.

Although the present invention and its advantages have been described in detail, it should be understood that various changes, substitutions, and alterations can be made herein without departing from the spirit and scope of the invention as defined by the appended claims.

What is claimed is:

1. A dynamic fluid loss cell apparatus, comprising:
    (a) a cell for receiving a first fluid and a core, wherein said core has a first side and a second side;
    (b) a pressurizing element operable for creating pressure differential between the first side and the second side;
    (c) a flow mechanism operable to flow said first fluid about the first side, the first fluid being selected from the group of a first drilling fluid, a second drilling fluid, and a spacer fluid; and
    (d) an acoustic measurement device operable to measure a first portion of the first drilling fluid on the first side, the measurement device including a transducer for transmitting a first acoustic signal and receiving a second acoustic signal.

2. The dynamic fluid loss cell apparatus of claim 1, further comprising a heating element operable to heat the first fluid.

3. The dynamic fluid loss cell apparatus of claim 1, further comprising a fluid discharge operable for flowing a portion of the first fluid from the second side to outside the cell.

4. The dynamic fluid loss cell apparatus of claim 1, wherein the flow mechanism comprises a rotating sleeve and a drive shaft.

5. The dynamic fluid loss cell apparatus of claim 1, wherein
    (a) the flow mechanism comprises a rotating sleeve and a drive shaft;
    (b) the rotating flow sleeve has an optical window; and
    (c) the measuring device is operably connected to an optical switch.

6. The dynamic fluid loss cell apparatus of claim 1, further comprising:
    (a) a heating element to heat the first fluid; and
    (b) a fluid discharge operable to flowing a portion of the first fluid from the second side to outside the cell.

7. A method for dynamically simulating fluid loss in a well-bore, comprising:
   (a) receiving a core into a cell, wherein said core has a first side and a second side;
   (b) receiving a first fluid into the cell;
   (c) creating a pressure differential between the first side and the second side;
   (d) flowing the first fluid about the first side bv rotating a rotating sleeve having an acoustic window and transmitting a first acoustic signal through the acoustic window; and
   (e) acoustically measuring a layer of particles on the first side.

8. The method for dynamically simulating fluid loss in a well-bore of claim 7, further comprising:
   (a) flowing a portion of the first fluid from the second side and outside said cell; and
   (b) measuring the portion of the first fluid.

9. The method for dynamically simulating fluid loss in a well-bore of claim 7, wherein said acoustically measuring the layer of particles comprises:
   (a) receiving a second acoustic signal; and
   (b) separating the first acoustic signal from the second acoustic signal.

10. The method for dynamically simulating fluid loss in a well-bore of claim 7, further comprising building-up a first layer of particles on the first side with the first fluid, wherein the first fluid is a drilling fluid.

11. The method for dynamically simulating fluid loss in a well-bore of claim 10, further comprising removing the first layer of particles on the first side with a spacer fluid.

12. The method for dynamically simulating fluid loss in a wellbore of claim 11, further comprising:
   (a) flowing a portion of the first fluid from the second side and outside said cell, and
   (b) measuring the portion of the first fluid.

13. The method for dynamically simulating fluid loss in a well-bore of claim 7, further comprising removing a first layer of particles on the first side with the first fluid, wherein the first fluid is a spacer fluid.

14. A dynamic fluid loss cell apparatus, comprising:
   (a) a cell for receiving a core and a first fluid, wherein said core has a first side and a second side and said first fluid is selected from the group of a drilling fluid and a spacer fluid;
   (b) a pressurizing element for creating a pressure differential between the first side and the second side;
   (c) a rotating sleeve about the core, wherein the rotating sleeve has an acoustic window;
   (d) a transducer for transmitting a first acoustic signal and receiving a second acoustic signal to measure a filter-cake layer;
   (e) a delay line separating the transducer and the first fluid;
   (f) a fluid discharge operable for flowing a portion of the first fluid from the second side to outside the cell; and
   (g) an optical switch operably connected to the transducer.

15. The dynamic fluid loss cell apparatus of claim 14, further comprising a heating element to heat the first fluid.

16. The dynamic fluid loss cell apparatus of claim 14, wherein the transducer measures a thickness of the filter-cake layer.

17. The dynamic fluid loss cell apparatus of claim 14, further comprising:
   a flow mechanism operable to flow said first fluid about the first side.

* * * * *